United States Patent [19]
Cavalieri et al.

[11] Patent Number: 5,952,183
[45] Date of Patent: Sep. 14, 1999

[54] SYNTHESIS OF ESTROGEN-PURINE BASE AND ESTROGEN-MERCAPTURATE ADDUCTS AND DEVELOPMENT OF FLUORESCENT PROBES AND MONOCLONAL ANTIBODIES TO ASSAY THOSE ADDUCTS

[76] Inventors: Ercole L. Cavalieri, 22635 Wilson Ave., Waterloo, Nebr. 68069; George P. Casale, 6718 S. 145th St., Omaha, Nebr. 68137; Eleanor G. Rogan, 8210 Bowie Dr., Omaha, Nebr. 68114; Douglas E. Stack, 4818 Orchard Ave., Omaha, Nebr. 68117

[21] Appl. No.: 09/060,586

[22] Filed: Apr. 15, 1998

Related U.S. Application Data

[62] Division of application No. 08/634,941, Apr. 19, 1996, Pat. No. 5,840,889.

[51] Int. Cl.$^6$ .................................................. G01N 33/53
[52] U.S. Cl. ........................ 435/7.1; 530/387.1; 544/264
[58] Field of Search ......................... 435/7.1; 530/387.1; 544/264

[56] References Cited

PUBLICATIONS

Abul–Hajj, Y. et al., "An Estrogen–Nucleic Acid Adduct. Electroreductive Intermolecular Coupling of 3,4–Estrone–o– quinone and Adenine", *J. Am. Chem. Soc.*, 117:6144–6145 (1995).

Liehr, J., "Mechanisms of Metabolic Activation and Inactivation of Catecholestrogens: A Basis of Genotoxicity", *Polycyclic Aromatic Compounds*, 6(10):229–239 (1994), Gordon and Breach Science Publishers S.A.

Han, X, "Microsome–mediated 8–hydroxylation of guanine bases of DNA by steroid estrogens: correlation of DNA damage by free radicals with metabolic activation of quinones", *Carcinogenesis*, 16(10) 2571–2574 (1995).

Pierce Chemical Co. Immunotechnology catalog & handbook. 1992, pp. 39–40.

Fujji et al., "Characterization of antisera to 2–hydroxyestradiol and 4–hydroxyestradiol using 6–(0–carboxymethyl)oxime–and 17–hemisuccinate–bovine serum albumin conjugates in radioimmunoassay", *Steroids*, 46(4,5) 857–865 (1985).

Numazawa et al., "Radioimmunoassay of 2–hydroxyestrone using antisera raised against antigenic complexes obtained by convenient methods", *Chem. Pharm. Bull*, 37(6) 1561–1563 (1989).

Knuppen, et al., "Enzymatic mathylation of thioethers of 2–hydroxyoestradiol by human and rat liver in vitro", *Hoppe–Seyler's Z. Physiol. Chem.*, 353:565–568 (1972).

Jellinck et al., "Synthesis of estrogen glutathione and cysteine derivatives", *Steroids*, 13(5) 711–718 (1969).

Numazawa et al., "Occurrence of Cysteine Conjugate of 2–Hydroxyestrone in Rat Bile, with Special Reference to Its Formation Mechanism", *Chem. Pharm. Bull.*, 22(3) 663–668 (1974).

Suzuki, E et al., "Synthesis of N–acetylcysteine conjugates of catechol estrogens", *Steroids*, 61:296–301 (May, 1996).

Stack, et al., Genotoxic mechanisms of catechol estrogens; Depurinating adducts and tumor initiation, *Proc. Am. Assoc. for Cancer Res.* 37:129 #893 (Mar. 1996) (abstract).

*Primary Examiner*—Paula K. Hutzell
*Assistant Examiner*—Minh-Tam Davis
*Attorney, Agent, or Firm*—Zarley, McKee, Thomte, Vorhees & Sease

[57] ABSTRACT

Estrogen-nucleoside, estrogen-guanine and estrogen-mercapturate adducts are potential biomarkers for determining susceptibility of animals to a number of estrogen related cancers. These adducts may be used as biomarkers for determining risk of estrogen-induced cancers. A linker chemistry has been devised to couple these adducts to protein for production of immunogens, required for production of specific monoclonal antibodies.

4 Claims, 2 Drawing Sheets

SYNTHESIS OF ESTROGEN-PURINE BASE AND ESTROGEN-MERCAPTURATE ADDUCTS AND DEVELOPMENT OF FLUORESCENT PROBES AND MONOCLONAL ANTIBODIES TO ASSAY THOSE ADDUCTS

This is a divisional of commonly owned application Ser. No. 08/634,941 filed on Apr. 19, 1996, now U.S. Pat. No. 5,840,889.

GRANT REFERENCE CLAUSE

This invention was made with government support under PO1-CA-49210 and F32-CA-65084 awarded by the National Cancer Institute. The government has certain rights in this invention.

BACKGROUND OF THE INVENTION

Estrogen is a hormone secreted in major quantities by the ovaries. The principal function of estrogens is to cause cellular proliferation and growth of the tissues of the sexual organs and of other tissues related to reproduction. Estrogens exert their effects primarily on the fallopian tubes, breasts, skeleton, protein deposition, metabolism, fat deposition, hair distribution, skin, and electrolyte balance. While the exact mechanism has yet to be identified, estrogens have been known for many years to also play a role in the proliferation of certain types of cancer.

Three estrogens are present in significant quantities in the plasma of females: 17β-estradiol, estrone, and estriol which have the following formulas:

The principal estrogen secreted by the ovaries is 17β-estradiol. Small amounts of estrone are also secreted, but most of this is formed in the peripheral tissues from androgens secreted by the adrenal cortices and by the ovarian thecal and stromal cells. Estriol is an oxidative product derived from both estradiol and estrone, the conversion occurring mainly in the liver.

Estrogen degradation takes place in the liver wherein the liver conjugates the estrogens to form glucuronides and sulfates, and about one-fifth of these conjugated products are excreted in the bile while most of the remainder are excreted in the urine. Also, the liver converts the potent estrogens, estradiol and estrone, into the almost totally inactive estrogen estriol.

In mammalian cells, the estrogens 17β-estradiol ($E_2$) and estrone ($E_1$), which are continuously interconverted by 17β-oxidoreductase, are generally metabolized via two major pathways: hydroxylation at the 16α-position or hydroxylation at the 2- or 4-position by cytochrome P-450. The latter pathway produces catechol estrogens (CE).

CE are typically conjugated by catechol-O-methyltransferases to give their monomethoxy derivatives. These enzymes are protective, because only non-methylated CE can be oxidized to their quinones (CE-Q) by peroxidases and cytochrome P-450.

Once CE form quinones, they can be acted upon by glutathione to form estrogen-glutathione adducts. These adducts in turn are broken down in the kidneys to produce cysteine and N-acetylcysteine adducts. The cysteine/N-acetylcysteine adducts are then secreted in the urine.

The role of estrogens in the induction of cancer has generally been related to stimulation of proliferation by receptor-mediated processes. Nandi, S. et al. (1995), "Hormones and Mammary Carcinogenesis in Mice, Rats, and Humans: A Unifying Hypothesis." *Proc. Natl. Acad. Sci. USA*, 92, 3650–3657. Estrogens can also play another important role by generating electrophilic species that can covalently bind to DNA to initiate cancer. Liehr J. G. (1990), "Genotoxic Effects of Estrogen." *Mutat. Res.* 238, 269–276. The present inventors have found evidence that CE-Q are the ultimate carcinogenic forms of estrogens, since these electrophiles can covalently bind to nucleophilic groups on DNA via a Michael addition. Furthermore, redox cycling generated by reduction of CE-Q to semiquinones and subsequent oxidation back to CE-Q can generate hydroxyl radicals that can cause additional DNA damage as proposed by Liehr et al. and Nutter et al. Liehr, J. G. et al. (1986) "Cytochrome P-450-Mediated Redox Cycling of Estrogen". *J. Biol. Chem.* 261, 16865–16870. Mutter, L. M., et al. (1994) "An o-Quinone Form of Estrogen Produces Free Radicals in Human Breast Cancer Cells: Correlation With DNA Damage." *Chem. Res. Toxicol.* 7, 23–28.

Several lines of evidence suggest that the 4-hydroxyCE are critical intermediates in the pathway leading to estrogen-induced cancer. Malignant renal tumors are induced in Syrian golden hamsters by treatment with $E_1$ or $E_2$, suggesting that $E_1$ or $E_2$ can be procarcinogenic compounds. Li, J. J. et al., (1983) "Relative Carcinogenic Activity of Various Synthetic and Natural Estrogens in the Syrian Hamster Kidney". *Cancer Res.* 43, 5200–5204. The CE 4-hydroxyestrone (4-$OHE_1$) and 4-hydroxyestradiol (4-$OHE_2$) also induce renal tumors in hamsters, whereas the corresponding 2-OH isomers do not. Liehr, J. G. et al., (1986), "Carcinogenicity of Catechol Estrogens in Syrian Hamsters", *J. Steroid. Biochem.* 24, 353–356. Furthermore, an estrogen-4-hydroxylase activity has been identified not only in hamster kidneys, but also in other organs prone to estrogen induced cancer, such as rat pituitary, mouse uterus, human MCF-7 breast cancer cells, human uterine myometrial tumors and human breast cancer tissues. Ricci, M. J., et al., (1995), "Predominant 4-Hydroxylation of Estradiol by Microsomes of Neoplastic Human Breast Tissue", *Proc. Amer. Assoc. Cancer Res.* 36, 255.

Adducts formed by direct reaction of CE-Q with DNA have been compared to those formed after activation of CE by horseradish peroxidase. Dwivedy, I. et al., (1992), "Synthesis and Characterization of Estrogen 2,3- and 3,4-quinones. Comparison of DNA Adducts Formed by the Quinones Versus Horseradish Peroxidase-Activated Catechol Estrogens". *Chem. Res. Toxicol.* 5, 828–833. In these studies, however, the structures of adducts were not identified.

The inventors have further evidence that the detection of N-acetylcysteine-estrogen and cysteine-estrogen adducts are also useful biomarkers for determining an individual's susceptibility to estrogen-related forms of cancer. Further, reactions of CE-Q with nucleosides and cysteine would provide authentic adducts and valuable insight into the mechanism of their formation. By studying the formation of these adducts, the mechanism behind estrogen-induced cancer would be more easily identified, thereby providing a means of diagnosing people at risk for estrogen-induced cancer, as well as aiding in the detection and treatment of estrogen-induced cancer. In addition, the synthetic adducts would serve as standard compounds for elucidating adducts formed by reaction of estrogen metabolites with DNA and glutathione.

It is therefore an object of the present invention to provide synthetic estrogen-purine base and estrogen-mercapturate adducts.

It is a further object of the present invention to provide diagnostic methods for detecting the presence of estrogen-purine base and estrogen-mercapturate adducts.

It is a further object of the present invention to provide fluorescent derivatives of the estrogen-purine base and estrogen-mercapturate adducts for use in fluorescent detection of those adducts.

It is still a further object of the present invention to provide a chemical test for detecting the presence of estrogen-purine base and estrogen-mercapturate adducts in body fluid samples.

It is yet another object of the present invention to provide an immunoaffinity matrix for purifying estrogen-purine base and estrogen-mercapturate adducts from body fluid samples for analysis by high performance liquid chromatography.

A further object of the present invention is to provide specific antibodies and capture agents for use in immunoassays for naturally occurring estrogen-purine base and estrogen-mercapturate adducts.

It is yet another object of the present invention to provide a method for detecting estrogen-induced cancer by assaying for the presence of estrogen-purine base and estrogen-mercapturate adducts in a body fluid sample.

It is yet another object of the present invention to provide synthetic antigens comprising estrogen-purine base and estrogen-mercapturate adducts.

It is still another object of the present invention to provide monoclonal antibodies which recognize the synthetic antigens comprising estrogen-purine base and estrogen-mercapturate adducts.

These and other objects of this invention are described more fully hereinafter.

SUMMARY OF THE INVENTION

This invention relates to estrogen-purine base and estrogen-mercapturate adducts which may be used in the detection, prevention, and treatment of estrogen-related cancers. One embodiment of the invention encompasses a fluorescence assay for the identification of biologically formed estrogen-purine base and estrogen-mercapturate adducts. This requires derivatization of the synthetic adducts with a fluorescent probe, dansyl chloride.

Another embodiment of the invention encompasses an immunoassay for the identification of biologically formed estrogen-purine base and estrogen-mercapturate adducts. This requires the preparation of synthetic adducts. Since these adducts are too small to be capable of producing antibodies, each must be linked to an immunogenic protein and the resultant antigenic conjugate used to produce specific antibodies for use in immunoassays of the native adducts present in biological fluid.

A third embodiment of the invention provides synthetic estrogen-purine base or estrogen-mercapturate adducts. These adducts when linked to an immunogenic protein carrier comprise the haptenic portion of the resulting conjugate. These adducts are useful for providing insight into the type of DNA damage that can be caused by ortho-quinones of the catechol estrogens.

A further embodiment of the present invention involves the production of monoclonal antibodies and capture agents for use in immunoassays for naturally occurring estrogen-purine base and estrogen-mercapturate adducts. These monoclonal antibodies are useful for detecting these adducts as a means of determining susceptibility to estrogen-induced cancer and as a means of diagnosing and treating such estrogen-induced cancer.

DETAILED DESCRIPTION OF THE PREFERRED EMBODIMENT

Estrogen Adducts

In accordance with one embodiment of this invention there are provided synthetic adducts of estrogen and a purine base which is the purine base guanine (Gua) or the deoxyribonucleosides deoxyadenosine (dA) or deoxyguanosine (dG), or an adduct consisting of estrogen and a mercapturate which is cysteine or N-acetylcysteine. These adducts exist naturally in the body and have now been discovered to be useful as biomarkers for determining the susceptibility to a number of human cancers. These adducts when conjugated to an immunogenic protein as discussed hereinafter, form the haptenic portion of the novel conjugates of this invention.

The estrogen used in the present invention can be from any natural or artificial source. Natural estrogens are produced in major quantities by the ovaries and in minor amounts by the adrenal cortices. Synthetic sources of estrogen are well known in the art and are used in a variety of prescription medications for treatment of menopausal symptoms and for birth control, for example. The only requirement of the estrogen source is its metabolism to CE-Q and its capability of adduction to DNA and/or glutathione. The preferred forms of estrogen are estrone ($E_1$) and 17β-estradiol ($E_2$)

The estrogen-purine base adducts of the present invention have three general formulas (Formulas 1A–1C):

FORMULA 1A

Wherein X is oxo (=O) or hydroxy (—OH). The compounds of Formula 1A comprise 7[4-hydroxyestron-1(α,β)-yl]guanine and 7[4-hydroxyestradiol-1(α,β)-yl]guanine, wherein $E_1$ is estrone (R is =O) and $E_2$ is estradiol (R is —OH). For simplicity, these compounds may be conveniently referred to as 4-$OHE_1$-1(α,β)-N7Gua and 4-$OHE_2$-1(α,β)-N7Gua.

FORMULA 1B

Wherein X is oxo or hydroxy. The compounds of Formula 1B are $N^2$[2-hydroxyestron-6-yl]deoxyguanosine and $N^2$[2-hydroxyestradiol-6-yl]deoxyguanosine (2-$OHE_1$-6-$N^2$dG and 2-$OHE_2$-6-$N^2$dG).

FORMULA 1C

Wherein X is oxo or hydroxy. The compounds of Formula 1C are $N^6$[2-hydroxyestron-6-yl]deoxyadenosine and $N^6$[2-hydroxyestradiol-6-yl]deoxyadenosine (2-$OHE_1$-6-$N^6$dA and 2-$OHE_2$-6-$N^6$dA).

The estrogen-mercapturate adducts of the present invention have the following formulas (Formulas 2A–2C):

FORMULA 2A

Wherein X is oxo or hydroxy and R is hydrogen or acetyl. The compounds of Formula 2A are 4-hydroxyestron-2-yl-cysteine, 4-hydroxyestradiol-2-yl-cysteine, 4-hydroxyestron-2-yl-N-acetylcysteine, and 4-hydroxyestradiol-2-yl-N-acetylcysteine (4-$OHE_1$-2-Cys, 4-$OHE_1$-2-(NAc)Cys, 4-$OHE_2$-2-Cys, and 4-$OHE_2$-(NAc)Cys).

FORMULA 2B

Wherein X is oxo or hydroxy and R is hydrogen or acetyl. The compounds of Formula 2B are 2-hydroxyestron-1-yl-cysteine, 2-hydroxyestradiol-1-yl-cysteine, 2-hydroxyestron-1-yl-N-acetyl cysteine, and 2-hydroxyestradiol-1-yl-N-acetyl cysteine (2-OHE$_1$-1-Cys, 2-OHE$_2$-1-Cys, 2-OHE$_1$-1(NAc)Cys, and 2-OHE$_2$-1-(NAc)Cys).

FORMULA 2C

Wherein X is oxo or hydroxy and R is hydrogen or acetyl. The compounds of Formula 2C are 2-hydroxyestron-4-yl-cysteine, 2-hydroxyestradiol-4-yl-cysteine, 2-hydroxyestron-4-yl-N-acetylcysteine, and 2-hydroxyestradiol-4-yl-N-acetylcysteine (2-OHE$_1$-4-Cys, 2-OHE$_2$-4-Cys, 2-OHE$_1$-4-(NAc)Cys, and 2-OHE$_2$-4-(NAc)Cys).

Estrogen Adduct-Fluorescent Probes

One method of analyzing estrogen-purine adducts and estrogen-mercapturate adducts is to couple these adducts with the fluorescent probe dansyl chloride. This allows sensitive detection of the adducts with a fluorescence monitor during separation by high pressure liquid chromatography (HPLC). The estrogen-purine base or estrogen-mercapturate adduct is reacted with dansyl chloride in acetone under basic conditions. The adducts derivatized with the fluorescent probe have four general formulas (Formulas 3A–3D):

FORMULA 3A

Wherein X is oxo or hydroxy. The compounds of Formula 3A are 3-hydroxy,4-hydroxy,N$^2$Gua-tridansyl-7[4-hydroxyestron-1($\alpha,\beta$)-yl]guanine and 3-hydroxy,4-hydroxy, N2Gua-tridansyl-7[4-hydroxyestradiol-1($\alpha,\beta$)-yl]guanine [3-OH,4-OH, N$^2$Gua-tridansyl-E$_1$-1($\alpha,\beta$)-N7Gua and 3-OH,4-OH,N$^2$Gua-tridansyl-E$_2$-1($\alpha,\beta$)-N7Gua].

FORMULA 3B

Wherein X is oxo or hydroxy and R is hydrogen or acetyl. The compounds of Formula 3B are 3-hydroxy,4-hydroxy-didansyl-4-hydroxyestron-2-yl-cysteine, 3-hydroxy,4-hydroxy-didansyl-4-hydroxyestradiol-2-yl-cysteine, 3-hydroxy,4-hydroxy-didansyl-4-hydroxyestron-2-yl-N-acetylcysteine and 3-hydroxy,4-hydroxy-didansyl-4-hydroxyestradiol-2-yl-N-acetylcysteine [3-OH,4-OH-didansyl-$E_1$-2-Cys and 3-OH,4-OH-didansyl-$E_2$-2-Cys, 3-OH,4-OH-didansyl-$E_1$-2-(NAc)Cys and 3-OH,4-OH-didansyl-$E_2$-2-(NAc)Cys].

FORMULA 3C

Wherein X is oxo or hydroxy and R is hydrogen or acetyl. The compounds of Formula 3C are 2-hydroxy,3-hydroxy-didansyl-2-hydroxyestron-1-yl-cysteine, 2-hydroxy,3-hydroxy-didansyl-2-hydroxyestradiol-1-yl-cysteine, 2-hydroxy,3-hydroxy-didansyl-2-hydroxyestron-1-yl-N-acetylcysteine and 2-hydroxy,3-hydroxy-didansyl-2-hydroxyestradiol-1-yl-N-acetylcysteine [2-OH,3-OH-didansyl-$E_1$-1-Cys and 2-OH,3-OH-didansyl-$E_2$-1-Cys, 2-OH,3-OH-didansyl-$E_1$-1-(NAc)Cys and 2-OH,3-OH-didansyl-$E_2$-1-(NAc)Cys].

FORMULA 3D

Wherein X is oxo or hydroxy and R is hydrogen or acetyl. The compounds of Formula 3D are 2-hydroxy,3-hydroxy-didansyl-2-hydroxyestron-4-yl-cysteine, 2-hydroxy,3-hydroxy-didansyl-2-hydroxyestradiol-4-yl-cysteine, 2-hydroxy,3-hydroxy-didansyl-2-hydroxyestron-4-yl-N-acetylcysteine and 2-hydroxy,3-hydroxy-didansyl-2-hydroxyestradiol-4-yl-N-acetylcysteine [2-OH,3-OH-didansyl-$E_1$-4-Cys and 2-OH,3-OH-didansyl-$E_2$-4-Cys, 2-OH,3-OH-didansyl-$E_1$-4-(NAc)Cys and 2-OH,3-OH-didansyl-$E_2$-4-(NAc)Cys].

Estrogen Adduct-Linker Complexes

In addition to the above synthetic adducts, the present invention provides synthetic antigens useful in raising antibodies specific to the novel synthetic adducts of this invention. The antigen comprises a hapten, which is a synthetic adduct of this invention, covalently bound to an immunogenicity-conferring carrier, wherein, in the antigen molecule, all the functional groups of the hapten are free to exert their antigenic determinacy. Preferably, the carrier (generally a protein or polypeptide) is itself immunogenic, and a substantial plurality of hapten moieties are coupled to a single carrier moiety. The number of hapten molecules actually bound to the carrier is a function of the physical and chemical features of the carrier. As an example, for antigenically effective conjugates with native protein (polypeptide) carriers, the number of hapten moieties coupled to a single protein (polypeptide) molecule and the molecular weight of the protein (polypeptide) approximates a log/log relationship in which one to five haptens are coupled to a polypeptide of $10^3$ daltons, 5 to 10 haptens to a polypeptide of $10^4$ daltons, 25 to 30 haptens to a protein of $10^5$ daltons, 75 to 125 haptens to a protein of $10^6$ daltons. Exemplary are ovalbumin (4.5 times $10^4$ daltons), bovine serum albumin (6.8 times $10^4$ daltons) and keyhole limpet hemocyanin (4.5 to 13 times $10^6$ daltons) coupled with 15 to 20, 20 to 25, and 300 to 500 hapten moieties, respectively.

Generally, in synthesizing the antigen, a linking agent is used. The linking agent can have two functional groups, the first to be coupled with the adducts, and the second to be coupled with the carrier. According to the present invention, a particular adduct target compound (ultimately to be assayed) is selected as a hapten to form an antigen which is then used to form antibodies for use in the immunochemical assay of adducts and in the immunoaffinity purification of the adducts in biological samples. In one embodiment, these haptens can be represented by the structures of formulas 1A and 2A–2C above. Hereinafter, the term "adduct" is used to designate one of the compounds represented by formulas 1A and 2A–2C.

One method of the present invention encompasses preparing a synthetic antigen which is an adduct (hapten) coupled to a carrier. The method comprises the steps of derivatizing the synthetic adduct and coupling the derivatized adduct to the carrier. The carrier can be any macromolecule capable of conferring antigenicity, such as the protein hen ovalbumin (OA). In one example of this method, the enolate form of 4-OHE$_1$-1($\alpha$,$\beta$)-N7Gua is derivatized at the C-16 position by reaction with 4-N-maleimidomethyl-cyclohexane-1-carboxylester (MCC ester) in tetrahydrofuran. This derivatized adduct, which is a mixture of the $\alpha$ and $\beta$ isomers, is purified to give each isomer greater than 99% purity by reverse phase liquid chromatography. Because the MCC linker is attached at the 16 position, these two conjugates will serve for developing monoclonal antibodies for the N7Gua adducts of both 4-OHE$_1$ and 4-OHE$_2$. The derivatized adduct will then be dissolved in dimethylsulfoxide and added to a solution of Traut's modified OA. In the latter, lysyl $\epsilon$-amino groups have been converted to free sulfhydryl (SH) groups that react with the maleimido moiety of MCC to form a thioether bond coupling the derivatized adduct to the protein carrier (OA). The antigenic adduct-carrier conjugates are separated from unreacted derivatized adduct by gel sieving chromatography or cold acetone precipitation.

Reaction sequences according to the invention generally are selective and give good yields. In particular, cross-reactions and isomer formation are not likely, so that isolation of the antigen from antigenically distinct materials is not unduly difficult as the probability of other antigenic materials being formed is low.

Thus, the present invention further comprises antigens of the formula:

$[R_1\text{->}C\text{-}L\text{-}]_n$-Carrier wherein "$R_1$->C" represents an adduct of this invention; "L" is a linkage moiety between the carrier and the adduct; the "carrier" is a macromolecule (generally protein) conferring antigenicity; and "n" is an integer not exceeding the number of available reactive coupling sites on the carrier. Accordingly, the antigen of this invention is the product of coupling a linking agent with the carrier and with the C-16 of the estrone moiety of the adduct.

The MCC linker adducts of the present invention have the following general formulations (Formulas 4A–4D):

FORMULA 4A

The compound of Formula 4A is 7[4-hydroxyestron-16 (α,β)-4'-N-maleimidomethyl-1'-carboxy-cyclohexane-1(α, β)-yl]guanine. This compound may be conveniently referred to as 4-OHE$_1$-16(α,β)-MCC-1(α,β)-N7Gua.

FORMULA 4B

Wherein R is hydrogen or acetyl. The compounds of Formula 4B are 4-hydroxyestron-16(α,β)-4'-N-maleimidomethyl-1'-carboxy-cyclohexane-2-cysteine and 4-hydroxyestron-16(α,β)-4'-N-maleimidomethyl-1'-carboxy-cyclohexane-2-N-acetylcysteine (4-OHE$_1$-16(α, β)-MCC-2-Cys and 4-OHE$_1$-16(α,β)-MCC-2-(NAc)Cys).

FORMULA 4C

Wherein R is hydrogen or acetyl. The compounds of Formula 4C are 2-hydroxyestron-16(α,β)-4'-N-maleimidomethyl-1'-carboxy-cyclohexane-1-cysteine and 2-hydroxyestron-16(α,β)-4'-N-maleimidomethyl-1'-carboxy-cyclohexane-1-N-acetylcysteine (OHE$_1$-16(α,β)-MCC-1-Cys and 2-OHE$_1$-16(α,β)-MCC-1-(NAc)Cys.

FORMULA 4D

Wherein R is hydrogen or acetyl. The compounds of Formula 4D are 2-hydroxyestron-16(α,β)-4'-N-maleimidomethyl-1'-carboxy-cyclohexane-4-cysteine and 2-hydroxyestron-16(α,β)-4'-N-maleimidomethyl-1'-carboxy-cyclohexane-4-N-acetylcysteine (2-OHE$_1$-16(α, β)-MCC-4-Cys, 2-OHE$_1$-16(α,β)-MCC-4-(NAc)Cys.

Antigenic Complexes

The requirements for immunogenicity are not fully understood. However, it appears for a molecule to be antigenic, it must have a certain complexity and a certain minimal molecular weight. Formerly, it was thought that the lower molecular weight limit to confer antigenicity was about 5,000 da. However, antigenicity has recently been demonstrated with molecules having molecular weights as low as 2,000 da. Molecular weights of 3,000 da and more appear to be more realistic as a lower limit for immunogenicity, and approximately 6,000 da or more is preferred.

Exemplary immunogenic carrier materials are those set forth in Cremer et al., "Methods in Immunology" (1963), W. A. Benjamin Inc., New York, pp. 65–113 and Harlow and Lane, "Antibodies: A Laboratory Manual" (1988), Cold Spring Harbor Laboratory, New York, p.5. These disclosures are herein incorporated by reference. The carrier material can be a natural or synthetic substance, provided that it is an antigen or a partial antigen. For example, the carrier material can be a protein, a glycoprotein, a nucleoprotein, a polypeptide, a polysaccharide, a lipopolysaccharide, or a polyamino acid. An example of an apparently incomplete antigen is the polypeptide, glucagon.

A preferred class of natural carrier materials is the proteins. Proteins can be expected to have a molecular weight in excess of 5,000 da, commonly in the range of from 34,000 to 5,000,000 da. Specific examples of such natural proteins are hen ovalbumin (OA), bovine serum albumin (BSA), keyhole limpet hemocyanin (KLH), horse gammaglobulin (HGG), and thyroglobin.

Exemplary of synthetic carrier is the polyamino acid, polylysine. Where the synthetic antigen comprises a partially antigenic carrier conjugated with a hapten, it will generally be desirable for the conjugate to have a molecular weight in excess of 6,000 da, although somewhat lower molecular weights may be useful.

Preferably, the natural carrier has some solubility in water or aqueous alcohol. Desirably, the carriers are nontoxic to the animals to be used for generating antibodies.

The carrier must have one or preferably a plurality of functional moieties by means of which it can be coupled. Of course, these groups can be introduced synthetically. Preferably, in practicing the present invention, a single carrier moiety should have a plurality of hapten moieties coupled to it, for example, from about 15 to 30 for a protein of 100,000 da. In general, the maximum possible number of haptenic moieties per carrier molecule is preferred. Subject to steric hindrance and reduced structural complexity (and consequently reduced antigenicity), the maximum number will be determined by the number of reactive coupling groups on the carrier. For example, with BSA, it appears that the maximum number of hapten moieties that can be coupled is between 25 and 50.

In preparing the antigens of the invention it is, as a practical matter, very desirable to obtain them with a high degree of purity. High antigen purity appears to be an important requisite for optimum antibody production. Accordingly, it is desirable for the process to provide for isolation of the antigen from antigenically distinct materials. The latter will normally be undesired large molecules that may compete with the target antigen and minimize production of the desired antibodies or induce cross-reactive antibodies of relatively low specificity or affinity for the adducts. A feature of the process of the invention is that it is designed to minimize the formation of such undesired antigenically distinct materials.

However, as a general objective, it is desirable to ensure that the derivatized adduct compound is substantially purified for the carrier-coupling step, and is especially purified of substances that could covalently couple to the carrier under the intended conditions. Purification can, for example, be effected by chromatography or fractional crystallization, preferably to a degree of >99%.

Removal of small molecule reactants and reaction products from the synthesized antigen is generally desirable. However, some small molecule substances may be useful, for example for pH control. Thus, a convenient end-product form in which to recover the antigen is, in a buffered aqueous solution which is suitable for direct administration to animals.

The process of the invention can accordingly include a number of purification steps using well-known techniques such as column chromatography, dialysis, cold organic solvent extraction, and recrystallization. Further, it will be generally desirable to use high purity reactants. For a natural protein carrier commercially available high purity fractions are desirable.

Synthetic Capture Complexes

In addition to the above synthetic antigens, the present invention provides synthetic capture complexes useful in detecting and characterizing antibodies raised against the novel synthetic adducts of this invention, and in competitive enzyme-linked immunosorbent (ELISA) or other solid-phase immunoassays that may be used in detection and quantitation of authentic adducts in biological samples. The capture complex comprises a hapten, which is a synthetic adduct of this invention, covalently bound to an adhesion molecule, wherein in the capture complex, the functional groups of the hapten are free to exert their specific interaction and binding with antibodies directed against the novel adducts of this invention. Preferably, the adhesion molecule (generally a protein, polypeptide or polyamino acid) is not a component of the synthetic antigens which elicit antibodies to the novel adducts of this invention, and a substantial plurality of hapten moieties are coupled to a single adhesion molecule moiety. The number of hapten molecules bound to a single adhesion molecule may not be as high as the number of haptens bound to a single carrier in the synthetic antigens of this invention and may be as low as one molecule for each adhesion molecule. In one embodiment of the capture complex, 5 to 10 hapten moieties are bound to a single molecule of the protein bovine serum albumin.

Generally, in synthesizing the capture complex, a linking agent is used. The linking agent can have two functional groups, the first to couple with the adduct, and the second to couple with the adhesion molecule. Generally, coupling of the linking agent to the adduct is through C-16 of estrone.

According to the present invention, a particular adduct target compound (ultimately to be assayed) is selected as a hapten to form the capture complex which is then used to detect and characterize antibodies formed against the same hapten used to form the antigen. These haptens can be represented by the structures of formulas 1A and 2A–2C above.

Thus, the present invention encompasses a capture complex, and a method of producing it, which is capable of interacting and binding specifically with the antibodies specific to an adduct of this invention.

One method of the present invention encompasses preparing a synthetic capture complex which is an adduct coupled to an adhesion molecule. The method comprises the steps of derivatizing the synthetic adduct at C-16 on $E_1$ and coupling the derivatized adduct to the adhesion molecule. The adhesion molecule can be any macromolecule capable of adhering to the solid phase of a solid phase immunoassay, such as the protein bovine serum albumin. In one example of this method, 4-$OHE_1$-1-($\alpha,\beta$)-N7Gua is derivatized at the C-16 position by reaction with 4-N-maleimidomethylcyclohexane-1-carboxylester (MCC ester) in tetrahydrofuran. This derivatized adduct which is a mixture of $\alpha$ and $\beta$ isomers is purified to give each isomer greater than 99% purity by reverse phase liquid chromatography. The derivatized adduct will then be dissolved in dimethylsulfoxide and added to a solution of Traut's modified bovine serum albumin (BSA). In the latter, lysyl $\epsilon$-amino groups have been converted to free sulfhydryl (SH) groups that react with the malemimido moiety of MCC to form a thioether bond coupling the derivatized adduct to the adhesion molecule (BSA). The adduct-adhesion molecule conjugates are separated from unreacted derivatized adduct by gel sieving chromatography or cold acetone precipitation.

Appropriate linking agents for use in the present invention include divalent residues derived from succinimidyl-4-(N-maleimidomethyl)cyclohexane-1-carboxylate, sulfosuccinimidyl-4-(N-maleimidomethyl)cyclohexane-1-carboxylate, N-$\gamma$-maleimidobutyryloxysuccinimide ester, N-$\gamma$-maleimidobutyryloxysulfosuccinimide ester or N-succiniuridyl-3(2-pyridyldithio)propionate.

Reaction sequences according to the invention generally are selective and give good yields. In particular isomers of target adducts are separated so that isolation of the antigen-specific capture complex from antigenically distinct materials is not unduly difficult as the probability of other antigenic materials being formed is low.

Thus, the present invention further comprises capture complexes of the formula:

[$R_1$->$C$-$L$-]$_n$-Adhesion Molecule where "$R_1$->$C$" represents an adduct of this invention; "L" is a linkage moiety between C-16 of the estrone group and the adhesion molecule; the "adhesion molecule" is a macromolecule (generally protein) conferring adhesiveness to the solid-phase of a solid phase immunoassay; and "n" is an integer not exceeding the number of available reactive coupling sites on the adhesion molecule.

Preparation of Anti-Adduct Antibodies

The present invention thus embodies a biomarker for determining susceptibility to a number of human cancers and a method of diagnosis, therapy or study of the same by assaying of this marker. The presence of the marker may be ascertained by collecting a biological sample which may include serum, plasma, urine, saliva, or other body fluids. A variety of techniques are known in the art to identify and/or quantify the marker's presence. One method involves exploitation of the immunogenicity of the marker when coupled with carrier protein, by developing monoclonal antibodies and immunological quantification. Conventional immunoassays are well known and readily ascertained by those of ordinary skill in the art.

Polyclonal antibodies can be raised by administration of an antigen of the invention to vertebrate animals, especially mammals such as goats or rabbits, using known immunization procedures. Usually a buffered solution of the antigen accompanied by Freund's adjuvant is injected subcutaneously at multiple sites. A number of such administrations at intervals of days or weeks is usually necessary. A number of animals, for example from 3 to 20, is so treated with the expectation that only a small proportion will product good antibodies. However, one can provide antibodies sufficient for thousands of assays. The antibodies are recovered from the animals after some weeks or months.

The use of monoclonal antibodies in the immunoassay embodiment of this invention is particularly preferred because they can be producted in large quantities and the product is homogeneous. Monoclonal antibodies are prepared by recovering lymph node or spleen cells from immunized animals and immortalizing the cells in conventional fashion, e.g., by fusion with myeloma cells or by Epstein-Barr virus transformation in screening for clones expressing the desired antibody. The hybridoma technique described originally by Koehler and Milstein, *Eur. J. Immunol.*, 6:511 (1976) by Hammerling et al., in "Monoclonal Antibodies and T-Cell Hybridomas", Elsevier, New York, pp. 563–681 (1981), and by Zola, in "Monoclonal Antibodies: A Manual of Techniques", CRC Press, Boca Raton, Fla. (1987) have been widely applied to produce hybrid cell lines that secrete high levels of monoclonal antibodies against many specific antigens. The hybrid cell lines can be maintained in vitro in cell culture media. The cell lines producing the antibodies can be selected and/or maintained in a medium containing hypoxanthine-aminopterin thymidine (HAT). In fact, once the hybridoma cell line is established, it can be maintained on a variety of nutritionally adequate media. Moreover, the hybrid cells lines can be stored and preserved in any number of conventional ways, including freezing and storage under liquid nitrogen. Frozen cell lines can be revived and cultured indefinitely with resumed synthesis and secretion of monoclonal antibody.

The secreted antibody is recovered from tissue culture supernatant or ascites fluid by conventional methods such as immune precipitation, ion exchange chromatography, affinity chromatography such as protein A/protein G column chromatography, or the like. The antibodies described herein are also recovered from hybridoma cell cultures by conventional methods such as precipitation with 50% ammonium sulfate. The purified antibodies can then be sterile filtered.

The term "monoclonal antibody" as used herein refers to any antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins.

The monoclonal antibodies herein also include hybrid and recombinant antibodies produced by splicing a variable (including hypervariable) domain of an anti-adduct antibody with a constant domain (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$ and Fv), so long as they exhibit the desired biological activity. (See e.g. Cabilly et al. U.S. Pat. No. 4,816,567; Mage and Lamoyi, "Monoclonal Antibody Production Technique and Applications", pp. 79–97 (Marcel Dekker, Inc., New York, 1987)).

Thus, the modifier "monoclonal" indicates the character of the antibody as being obtained from a substantially homogenous population of antibodies, and is not to be construed as requiring production of the antibody by any particular method. For example, the monoclonal antibodies to be used in accordance with the present invention may be made by the hybridoma method described by Koehler and Milstein, supra, or may be made by recombinant DNA methods (Cabilly, et al. supra).

Anti-estrogen adduct antibodies are useful in diagnostic assays for adduct expression in specific cells or tissues wherein the antibodies are labeled as described below and are immobilized on an insoluble matrix. Anti-estrogen adduct antibodies also are useful for the affinity purification of the adduct from recombinant cell culture or natural sources.

Immunoassays for Estrogen Adducts

Suitable diagnostic assays for the estrogen adducts are well known per se. For example, a biological sample may be assayed for estrogen adducts by obtaining the sample from a desired source, admixing the sample with anti-estrogen adduct antibody to allow the antibody to form antibody/adduct complex with any adduct present in the mixture and detecting any antibody/adduct complex present in the mixture. The biological sample may be prepared for assay by methods known in the art which are suitable for the particular sample. The methods of admixing the sample with antibodies and the methods of detecting antibody/adduct complexes are chosen according to the type of assay used. Such assays include competitive and sandwich assays. Sandwich methods employ a phase-separation step as an integral part of the method. Competitive assays may employ a phase-separation step or may be conducted in a single reaction mixture.

Analytical methods for the adducts all use one or more of the following reagents: labeled adduct analog, immobilized adduct analog, labeled anti-adduct antibody, immobilized anti-adduct antibody, adduct-adhesion molecule conjugate and steric conjugate.

The label used is any detectable functionality that does not interfere with the binding of adduct and anti-adduct antibody. Numerous labels are known for use in immunoassay, examples including moieties that may be detected directly, such as fluorochrome, chemiluminescent, and radioactive labels, as well as moieties such as enzymes, that must be reacted or derivatized to be detected. Examples of such labels include the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyn, umbelliferone, luceriferases, e.g. firefly lucifera and bacterial lucifera (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g. glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Conventional methods are available to bind these labels covalently to proteins or polypeptides. For instance, coupling agents such as dialdehydes, carbondiimides, dimaleimides, bisimidates, bisdiazotized benzidine, and the like may be used to tag antibodies with the above described fluorescent, chemiluminescent and enzyme labels. See for e.g. U.S. Pat. Nos. 3,940,475 (fluorimetry) and 3,645,090 (enzymes); Hunter et al., *Nature*, 144:945 (1962); David et al., *Biochemistry*, 13:1014–1021 (1974); Pain et al., *J. Immunol. Methods*, 40:219–230 (1981); and Nygren, *J. Histochem. and Cytochem.*, 30:407–412 (1982). Preferred labels herein are enzymes such as horseradish peroxidase and alkaline phosphatase.

The conjugation of such label, including the enzymes, to the antibody is a standard manipulative procedure for one of ordinary skill in immunoassay techniques. See for e.g. O'Sullivan et al., "Methods for the Preparation of Enzyme-Antibody Conjugates for use in Enzyme Immunoassays", in *Methods in Enzymology*, Et. J. J. Langone and H. VanVunkis, Vol. 73 (Academic Press, New York, N.Y., 1981), pp. 147–156.

Immobilization of reagents is required for certain assay methods. Immobilization entails separating the anti-estrogen adduct antibody from any adduct that remains free in solution. This conventionally is accomplished by either insolubilizing the anti-adduct antibody or adduct analogue before the assay procedure, as by adsorption to a water-insoluble matrix or surface (Bennich et al., U.S. Pat. No. 3,720,760), by covalent coupling (e.g., using glutaraldehyde cross-linking), or by insolubilizing the anti-adduct antibody or adduct analog afterward, e.g. by immunoprecipitation.

Other assay methods, known as competitive or sandwich assays, are well established and widely used in the commercial diagnostic industry.

One form of competitive assay relies on the ability of a tracer estrogen adduct analog to compete with the test sample adduct for a limited number of anti-adduct antibody antigen-binding sites. The anti-adduct antibody generally is insolubilized before or after the competition and then the tracer and adduct bound to the anti-adduct antibody are separated from the unbound tracer and adduct. This separation is accomplished by decanting (where the binding partner was preinsolubilized) or by centrifuging (where the binding partner was precipitated after the competitive reaction). The amount of test sample adduct is inversely proportional to the amount of bound tracer as measured by the amount of marker substance. Dose-response curves with known amounts of adduct are prepared and compared with the tests results to quantitatively determine the amount of adduct present in the test sample.

Another form of competitive assay relies on the ability of test sample adduct to bind with high affinity to a limited number of anti-adduct antibody antigen-binding sites and, thereby, reduce binding of the anti-adduct antibody to the adduct-adhesion complex (capture complex) adsorbed to a solid surface. The anti-adduct antibody generally is reacted first with test sample adduct. The mixture is then transferred to a multiwell plate, the wells of which were previously coated with adduct-adhesion complex. The degree of binding of anti-adduct antibody to the adduct-adhesion complex is inversely proportional to the amount of test sample adduct. Generally, bound anti-adduct antibody is detected with an enzyme-tagged polyclonal antibody specific for the anti-adduct antibody. These competitive assays are called competitive ELISAs.

Briefly, in a typical competitive assay, sample to be tested is brought into contact with a first antibody (i.e. an adduct-specific antibody of this invention). However, because most common assays are formulated for water-soluble haptens, the assays should be adapted to accommodate the hydrophobic nature of the adducts being measured in the test sample. To illustrate, water-soluble haptens typically are combined with antibodies in a buffer that contains additional proteins, at a concentration of about 1–10 mg/ml reaction mix. The presence of these additional proteins does not affect the binding of antibodies to water-soluble haptens, since they are dissolved in the aqueous medium and freely available for binding. By contrast, hydrophobic haptens tend to partition to hydrophobic domains of the additional proteins (e.g., each molecule of serum albumin possesses six large hydrophobic pockets), which interferes with their binding to antibodies in solution. Moreover, even in solutions having minimal additional protein, hydrophobic haptens tend to aggregate and precipitate from the reaction medium (this phenomenon increases with decreasing temperature).

To overcome the aforementioned difficulties associated with measuring hydrophobic haptens by competitive ELISA, several modifications have been developed in accordance with the present invention, which may be incorporated into standard ELISA techniques. These modifications are summarized below.

First, antibody solutions should be prepared to eliminate substantially all extraneous (non-antibody) proteins. This modification enhances antibody/adduct interaction by eliminating the possibility that hydrophobic adducts will become sequestered in hydrophobic regions of non-antibody proteins. To accomplish this with monoclonal antibodies (MAbs), for example, hybridomas are grown in a low serum medium (approx. 2%) in a high production tissue culture system (preferably producing up to about 50 mg MAb/day). MAbs (or other antibodies are purified by a two-step ammonium sulfate precipitation and by affinity chromatography on bioengineered Protein G ("protein A/G," Pierce, Rockford, Ill.). Additionally, conventional carrier/blocker proteins, such as BSA, are not included in the antibody/adduct reaction mixtures.

Second, antibody is diluted (approx. 1/500–1/5,000, depending on specific binding affinity) in an aqueous solution (e.g., Tris/NaCl) which contains no other protein.

Third, adduct is added in a small volume of DMSO (e.g., 10 $\mu$l in a typical reaction) to the vortexing antibody solution at room temperature.

Fourth, adduct/antibody mixtures are incubated at 37° C. for a period of time sufficient to allow formation of immune complexes between adduct present in the sample and the anti-adduct antibody (e.g., about 120 minutes), without further vortexing.

These reaction conditions increase the kinetic energy of both adduct and antibody, and disfavor aggregation of the adduct, thereby increasing availability of the adduct to antibody binding sites.

Another species of competitive assay called a "homogenous" assay, does not require a phase separation. Here, a conjugate of an enzyme with the adduct is prepared and used such that when anti-adduct antibodies bind to the adduct, the presence of the anti-adduct antibody modifies the enzyme activity. In this case, the adduct or its immunologically active fragments are conjugated with a bifunctional organic bridge to an enzyme such as peroxidase. Conjugates are selected for use with anti-adduct antibody so that binding of the anti-adduct antibody inhibits or potentiates the enzyme activity of the label. This method per se is widely practiced under the name of EMIT.

Steric conjugates are used in steric hindrance methods or homogenous assays. These conjugates are synthesized by covalently linking a low-molecular-weight hapten to a small adduct fragment so that antibody to hapten is substantially unable to bind the conjugate at the same time as the anti-adduct antibody. Under this assay procedure, the adduct present in the test sample will bind anti-adduct antibody, thereby allowing anti-hapten to bind the conjugate, resulting in a change in the character of the conjugate hapten, e.g. a change in fluorescence when the hapten is a fluorophore.

Immunoaffinity Purification of Estrogen Adducts

Estrogen adducts contemplated herein in individual serum, tissues, tissue extracts, or bodily fluids (e.g. urine) can be concentrated and purified by immunoaffinity procedures, in preparation for analyses by HPLC or other analytical methods. Immunoaffinity extraction of adducts from complex biological samples is rapid, yields quantitative recoveries of the adducts, and obviates complex extraction procedures and repeated cycles of chromatographic purification with significant losses of material. Anti-adduct antibodies are covalently coupled to a solid matrix such as agarose gel, generally in the form of beads 50–200$\mu$ in diameter. Typically, the support beads are derivatized with couplers including CNBr, N-hydroxysuccinimide and hydrazide. CNBr and N-hydroxysuccinimide form covalent bonds with primary amino groups of proteins, while hydrazide couples with aldehydes formed by periodate oxidation of the carbohydrate moiety of glycoproteins (e.g. antibodies). The latter is a preferable reaction which orients the antibodies with their binding sites projecting away from the support bead. The current art is such that the derivatization of the support gel and attachment of the antibodies are routine procedures as documented in Harlow and Lane, "Antibodies: A Laboratory Manual" (1988), Cold Spring Harbor Laboratory, New York, cp. 13.

According to one method, an antibody preparation consisting of 10–15 mg anti-adduct antibody in 3 mL of acetate buffer at pH 5.5 is oxidized by addition of 300 $\mu$L NaIO$_4$ solution (6.25 mg NAIO$_4$ per 300 $\mu$L acetate buffer). After one hour of reaction at room temperature, the oxidized antibody preparation is desalted with a gel-seiving column. Hydrazide-derivatized agarose-gel slurry, equivalent to 5 mL of packed volume, is added to a 50 mL plastic tube. The gel is washed with acetate buffer, then suspended to a final volume of 10 mL in acetate buffer. The 3-mL preparation of oxidized anti-adduct antibody is added to the gel suspension and incubated for 10–24 hours with agitation, at room temperature. Subsequently, the mixture is poured into a 1×10 cm column and any uncoupled antibody is washed away with phosphate-buffered saline at pH 7.0. The column is ready for concentration and purification of adduct present in biological samples.

Urine samples may be applied directly to the column or after dilution with phosphate-buffered saline. Volumes on the order of 100–400 mL may be applied to the column. After the sample has been applied, the column is washed with ca. 10 mL of phosphate-buffered saline. Purified, concentrated adduct is eluted from the column with phophate-buffered saline containing 20–50% (v/v) DMSO. The purified adduct is coupled with dansyl chloride, a fluorescent probe, in acetone under basic conditions. This allows sensitive fluorescence detection of the adducts after separation by high pressure liquid chromatography.

A number of terms and expressions are used throughout the specification and claims. In order to assure uniformity and avoid ambiguity, the following definitions are provided:

The term "estrogen" is intended to cover any form of estrogen found in the environment. These compounds are well known and have been described in the literature. Generally, these estrogens include β-estradiol, estrone, and estriol.

By the term "adduct" as used herein, means the covalent linkage of an estrogen molecule to either a purine nucleoside, base or a mercapturate.

By the term "depurination" is meant the metabolic removal of a purine-base adduct (as herein defined) from a DNA strand in which it was generated, leaving in its place an open (apurinic) site on the sugar-phosphate backbone. Those adducts which are susceptible to depurination are described as being "depurinating" adducts; those which remain bound to the DNA strand are described as being "stable" adducts.

All references cited in the specification are hereby expressly incorporated by reference. The following examples are offered by way of illustration and not by way of limitation.

EXAMPLE 1

Synthesis and Characterization of 4 Estrogen-purine Base Adducts

Chemicals. Synthesis of 4-OHE$_1$, 4-OHE$_2$ and 2-OHE$_2$ and the corresponding quinones was conducted by the following procedures of Dwivedy et al. The deoxyribonucleosides dG and dA were purchased from TCI (Portland, Oreg.) as the monohydrates and dried over P$_2$O$_5$ under vacuum at 100° C. for 48 h prior to use. All other chemicals were purchased from Aldrich Chemical Co. (Milwaukee, Wis.) and used without further purification.

HPLC. HPLC was conducted on Waters 600E solvent delivery system equipped with a Waters 990 photodiode array (PDA) detector interfaced with an APC-IV Powermate computer. Analytical separations were conducted by using a YMC ODS-AQ 5-$\mu$m, 120-Å column (6.0×250 mm) at a flow rate of 1 mL/min (YMC, Morris Plains, N.J.). The analytical gradient started with 30% CH$_3$OH in H$_2$O for 5 min., followed by a 60 min. linear gradient (CV6) to 100% CH$_3$OH. Preparative HPLC was conducted by using a YMC ODC-AQ 5-$\mu$m, 120-Å column (20×250 mm) at a flow rate of 6 mL/min. The preparative gradient started with 40% CH$_3$OH for 10 min, followed by a linear gradient (CV6) to 60% CH$_3$OH at 20 min, then held for 15 min.

A linear gradient to 100% CH$_3$OH was then conducted for 10 additional minutes, resulting in a total separation time of 45 min.

NMR. NMR spectra were recorded in dimethylsufoxide-d$_6$ (Me$_2$SO-d$_6$) at 25° C. on either a Varian XL-300 at 299.938 MHz or Varian Unity 500 at 499.835 MHz. Chemical shifts are reported relative to tetramethylsilane, which was employed as an internal reference. Nuclear Overhauser effect (NOE) spectra were obtained by subtracting a reference spectrum, recorded with the presaturation pulse off-resonance, from a spectrum recorded with a presaturation pulse on resonance.

All calculations were performed on a Silicon Graphics Iris Indigo 4000 workstation with the SYBYL 6.2 molecular modeling software (Tripos Assoc., St. Louis, Mo.). Structure optimization searches were performed by using the random conformation search provided by SYBYL. The number of "hits" for each conformer was set to 6, ensuring a 98.4% chance of finding all possible conformations. Each conformation was then minimized by using the Tripos force field with the Powell method of convergence. Energy vs. torsion angle data were obtained by the SYBYL gridsearch feature. Heats of formation were calculated with the PM3 semiempirical molecular orbital Hamiltonian (MOPAC 6.0, The Quantum Chemistry Program Exchange) performed through the SYBYL interface. Optimizations used the "precise ×100" in addition to the "MMOK" keyword for molecular mechanics correction to the guanine amide bond.

Mass Spectrometry

Exact mass measurements were conducted with a Kratos MS-50 triple analyzer tandem mass spectrometer equipped with a standard Kratos FAB source. The atom beam was 6–7 keV argon atoms at a total current of 1 mA at the cathode of the gun. A mixture of CsI and glycerol was used to generate reference-mass ions for the peak match mode.

Synthesis of Estrogen Nucleoside Adducts $E_1$-3,4-Q or $E_2$-3,4-Q+dG. A suspension of 4-OHE$_1$ or 4-OHE$_2$ (0.18 mmol) in 5 mL CH$_3$CN was cooled to 0° C. prior to the addition of activated MnO$_2$ (1.18 mmol). The suspension was stirred for 10 min, then filtered directly into a stirred solution of dG (0.94 mmol) in a solvent mixture of 10 mL CH$_3$CO$_2$H/H$_2$O (1:1). Aliquots were removed for HPLC analysis at 1, 2 and 4 h to monitor the course of the reaction. After 5 h at room temperature, solvents were removed under reduced pressure and the crude product was dissolved in a 1:1 solvent mixture of CH$_3$OH/dimethylformamide (DMF). The product was then isolated via preparative reverse phase HPLC, as described above, to afford 7[4-hydroxyestron-1($\alpha$,$\beta$)-yl]guanine]4-OHE$_1$-1($\alpha$,$\beta$)-N7Gua] or 7[4-hydroxyestradiol-1($\alpha$,$\beta$)-yl]guanine [4-OHE$_2$-1($\alpha$,$\beta$)-N7Gua] (40% yield).

4-OHE$_1$-1($\alpha$,$\beta$)-N7Gua. $^1$H and $^{13}$C NMR spectra showed the product to be a mixture of the $\alpha$ and $\beta$ isomers; the following spectra are those of the two isomers.

UV, $\lambda_{max}$ (nm): 211, 291. FTIR (KBr, cm$^{-1}$): 3430, 2920, 1745, 1700, 1630, 1570, 1480, 1200, 1150, 780. $^1$H NMR (500 MHz): 10.72 and 10.61 (bs, $^1$H, 1-NH[Gua], exchanged with D$_2$O), 9.44 and 9.43 (bs, 1H, 3OH, exchanged with D$_2$O), 8.50 and 8.49 (bs, 1H, 4OH exchanged with D$_2$O), 7.90 and 7.89 (s, 1H, 8-H[Gua]), 6.51 and 6.49 (s, 1H, 1-H and 2-H), 6.14 and 6.12 (bs, 2H, 2-NH$_2$[Gua], exchanged with D$_2$O), 2.89 (dd, J$_1$=17.5 Hz, J$_2$=4.0 Hz, 1H), 2.30–2.56(m, 3H), 1.96–2.02 (m, 1H), 1.83–1.90(m, 2H), 1.23–1.61(m, 4H), 1.10–1.21(m, 1H), 0.74–0.98(m, 2H), 0.74 (s, 3H, 13-CH$_3$), 0.45–0.68(m, 1H). $^{13}$C NMR (75 MHz): 162.2, 160.2, 159.9, 153.9, 153.8, 152.9, 152.8, 143.5, 143.2, 143.0, 142.8, 142.1, 142.0, 127.4, 126.3, 126.1, 125.8, 125.7, 113.6, 112.8, 109.3, 108.0, 49.7, 49.4, 47.3, 47.2, 44.2, 43.7, 35.7, 35.1, 32.3, 31.8, 30.7, 25.2, 25.1, 24.4, 24.3, 24.2, 21.1, 13.7, 13.6; MS, (M+H)$^+$ C$_{23}$H$_{26}$N$_5$O$_4$ calcd 436.19850, found 436.19863.

4-OHE$_2$-1($\alpha$,$\beta$)-N7Gua. $^1$H NMR spectrum showed the product to be a mixture of the $\alpha$ and $\beta$ isomers; the following spectra are those of the two isomers.

UV, $\lambda_{max}$ (nm): 211, 292. $^1$H NMR (500 MHz): 10.72 and 10.64 (bs, 1H, 1-NH[Gua], exchanged with D$_2$O), 9.38 and 9.36 (bs, 1H, 3-OH, exchanged with D$_2$O), 8.44 and 8.43 (bs, 1H, 4-OH, exchanged with D$_2$O), 7.89 and 7.88 (s, 1H, 8-H[Gua]), 6.48 and 6.46 (s, 1H, 1-H and 2-H), 6.13 and 6.11 (bs, 2H, 2-NH$_2$[Gua], exchanged with D$_2$O), 4.39 and 4.35(d, J=3.7, 1H, 17$\beta$-OH), 4.08(m, 1H, 17$\alpha$-H), 2.79(dd, J$_1$=17.0, H2, J$_2$=4.0 Hz, 1H), 2.30–2.56(m, 3H), 1.75–1.87 (m, 1H), 1.66–1.75(m, 1H), 1.46–1.57(m, 1H), 1.16–1.42 (m, 4H), 0.74 (s, 3H, 13-CH$_3$), 0.48–0.58(m, 1H). MS, (M+H) C$_{23}$H$_{28}$N$_5$O$_4$ calcd 438.21410, found 438.21410.

$E_1$-2,3-Q+dA. A suspension of 2-OHE$_1$ (0.18 mmol) in 5 mL CH$_3$CN was cooled to −40° C. prior to the addition of activated MnO$_2$ (1.18 mmol). The suspension was stirred for 10 min., then filtered directly into a stirred solution of dA (0.94 mmol) in a solvent mixture of 10 mL CH$_3$CO$_2$H/H$_2$O (1:1). Aliquots were removed for HPLC analysis at 1, 2 and 5 h to monitor the course of the reaction. After 5 h at room temperature, solvents were removed under reduced pressure, and the crude product was dissolved in 1:1 solvent mixture of CH$_3$OH/DMF. The product was then isolated via preparative reverse phase HPLC, as described above, to afford N6[ 2-hydroxyestron-6-yl]deoxyadenosine (2-OHE$_1$-6-N$^6$dA) (80% yield).

2-OHE$_1$-6-N$^6$dA. UV, $\lambda_{max}$ (nm): 207, 276. $^1$H NMR (300 MHz): 8.61(s, 1H, OH, exchanged with D$_2$O), 8.57(s, 1H, OH, exchanged with D$_2$O), 8.31 and 8.27(s and bs, 2H, 2-H and 8-H[dA]), 7.94(d, 2H, J=9.0 Hz, 6-NH[dA]), 6.68(s, 1H, 1-H), 6.56 (s, 1H, 4-H), 6.36(t, 1H, J=6.7 Hz, 1'-H[dA], 5.58(m, 1H, 6-H), 5.27(d, 1H, J=4.1 Hz, 3'-OH[dA], exchanged with D$_2$O), 5.17(t, 1H, J=6.0 Hz, 5'-OH[dA], exchanged with D$_2$O), 4.41(m, 1H, 3'-H[dA]), 3.88(m, 1H, 4'-H[dA]), 3.45–3.59 (m, 2H, 5'-H$_2$[dA]), 2.73(q, J=6.5 Hz, 1H), 2.38(dd, J$_1$=18.5 Hz, J$_2$=7.5 Hz, 1H), 2.19–2.27(m, 2H), 1.90–2.16(m, 4H), 1.89(t, J=9.0 Hz, 1H), 1.73–1.78(m, 1H), 1.56–1.67(m, 1H), 1.34–1.49(m, 3H), 0.81(s, 3H, 13-CH$_3$). MS (M+H)+C$_{28}$H$_{34}$N$_5$O$_5$ calcd 536.25090, found 536.25117.

$E_1$-2,3-Q+dG. A suspension of 2-OHE$_1$ (0.25 mmol) in 5 mL CH$_3$CN was cooled to −40° C. prior to the addition of activated MnO$_2$ (2.25 mmol). The suspension was stirred for 10 min, then filtered directly into a stirred solution of dG (1.30 mmol) in a solvent mixture of 10 mL CH$_3$CO$_2$H/H$_2$O (1:1). Aliquots were removed for HPLC analysis at 1, 2 and 5 h to monitor the course of the reaction. After 5 h at room temperature, solvents were removed under reduced pressure, and the crude product was dissolved in a 1:1 solvent mixture of CH$_3$OH/DMF. The product was then isolated via preparative reverse phase HPLC, as described above, to afford N$^2$[2-hydroxyestron-6-yl]deoxyguanosine (2-OHE$_1$-6-N$^2$dG) (10% yield).

2-OHE$_1$-6-N$^2$dG. UV, $\lambda_{max}$ (nm): 254, 287. $^1$H NMR (500 MHz): 9.92 (bs, 1H,1-NH[dG], exchanged with D$_2$O), 8.83 (bs, 2H, 2-OH and 3-OH, exchanged with D$_2$O), 7.91(2, 1H, 8-H[dG]), 6.84(d, 1H,2-NH[dG]), 6.69(s, 1H, 1-H), 6.64(s, 1H, 4-H), 6.18(t, 1H, J=6.7 Hz, 1'-H[dG]), 5.29(d, 1H, J=4.0 Hz, 3'-OH[dG], exchanged with D$_2$O), 4.99 (m, 1H, 6-H), 4.87(t, 1H, J=6.0 Hz, 5'-OH[dG], exchanged with D$_2$O), 4.38(m, 1H, 3'-H[dG]), 3.81(m, 1H, 4'-H[dG]), 3.49–3.58 (m, 2H, 5'-H2[dG]), 2.71(q, J=6.5 Hz, 1H), 2.41(dd, J$_1$=18.0 Hz, J$_2$=7.0 Hz, 1H), 2.16–2.28(m, 2H), 1.98–2.22(m, 3H), 1.85–1.96(m, 1H), 1.32–1.18(m, 6H), 0.85 (s, 3H, 13-CH$_3$). MS, (M+H)$^+$ C$_{28}$H$_{34}$N$_5$O$_7$ calcd 552.24580, found 552.24507.

RESULTS

Synthesis and Structure Determination of Estrogen Quinone Adducts formed with Deoxyribonucleosides Initial attempts to synthesize nucleoside adducts of estrogen quinones in aprotic solvents yielded no adducts. Neither dG nor dA reacted with $E_1$-3,4-Q or $E_1$-2,3-Q in DMF or Me$_2$SO. In acidic conditions, however, reaction of estrogen quinones with sulfur nucleophiles was previously reported. The solvent system CH$_3$CO$_2$H/H$_2$O (1:1) facilitated Michael addition of nucleophillic groups in dG and dA to both $E_1$-3,4-Q and $E_1$-2,3-Q, to give the products shown in Scheme II. No adducts were obtained with deoxycytidine or thymidine. The quinones were formed in CH$_3$CN at 0° C. for 4-OHE$_1$ and 4-OHE$_2$ and −40° C. for 2-OHE$_1$, and then filtered directly into a solution of the nucleoside previously dissolved in the 1:1 mixture of CH$_3$CO$_2$H/H$_2$O (ca. pH 2).

Reaction of $E_1$-3,4-Q with dG yielded a product that eluted as a single peak under several different HPLC conditions. Reaction yields were typically 40%. The reaction proceeded to completion after 5 h at room temperature and no other adducts were detected. NMR analysis showed the product to be a mixture of two conformational isomers attached to the C1 position of the estrogen A ring and the N7 position of guanine, 4-OHE$_1$-1($\alpha$,$\beta$)-N7Gua. The generation of two conformational isomers is the result of the rotational barrier about the C1-N7Gua bond. Thus, in one isomer, the guanine moiety is located primarily on the "$\alpha$" side of the estrogen ring system, 4-OHE$_1$-1$\alpha$-N7Gua, while the other isomer has the guanine moiety located on the "$\beta$" side of the estrogen ring system, 4-OHE$_1$-1$\beta$-N7Gua. Rotation from the $\alpha$ isomer to the $\beta$ isomer would involve the C8-Gua proton occupying the same Van der Waals radius as the C11 protons of the estrogen B ring. Energy as a function of the torsion angle about C10, C1, N7-Gua and C8-Gua shows a rotation barrier of 551 kcal/mol. The two isomers were formed in a ratio (via $^1$H-NMR) of 60% $\beta$ and 40% $\alpha$. The predominance of the $\beta$ isomers indicates formation of this adduct is under kinetic control, since calculations show the $\alpha$ isomer is thermodynamically more stable than the $\beta$ isomer. Molecular mechanical calculations, $\Delta E_{\alpha,\beta}=-5.9$ kcal/mol, and semiempirical quantum mechanical calulations, $\Delta Hf_{\alpha,\beta}=-2.9$ kcal/mol show the $\alpha$ isomer to be the more stable form. Attack of the nitrogen nucleoophile at C1 is the result of a 1,4-addition with respect to the C3 carbonyl. This is in contrast to sulfur nucleophiles, which attack at the C1 position, a 1,6-addition with respect to the C4 carbonyl. Molecular orbital calculations (semiempirical), PM3 Hamiltonian) have shown that in the neutral species, C1 bears more positive charge than C2 and that the lowest unoccupied molecular orbital (LUMO) has a higher coefficient at C2 than C1. Thus, soft electrophiles, such as thiols, will attack at C2, while harder electrophiles, such as nitrogen and oxygen, will attack C1. When molecular orbital calculations are done on protonated E$_1$-3,4-Q (i.e. acidic conditions), the regioselective attack on C1 by hard electrophiles is enhanced.

E$_1$-3,4-Q did not react with dA. With this nucleoside, only gradual decomposition of the quinone was observed. Reaction of E$_2$-3,4-Q with dG and dA produced the same results as E$_1$-3,4-Q.

Figure 1:
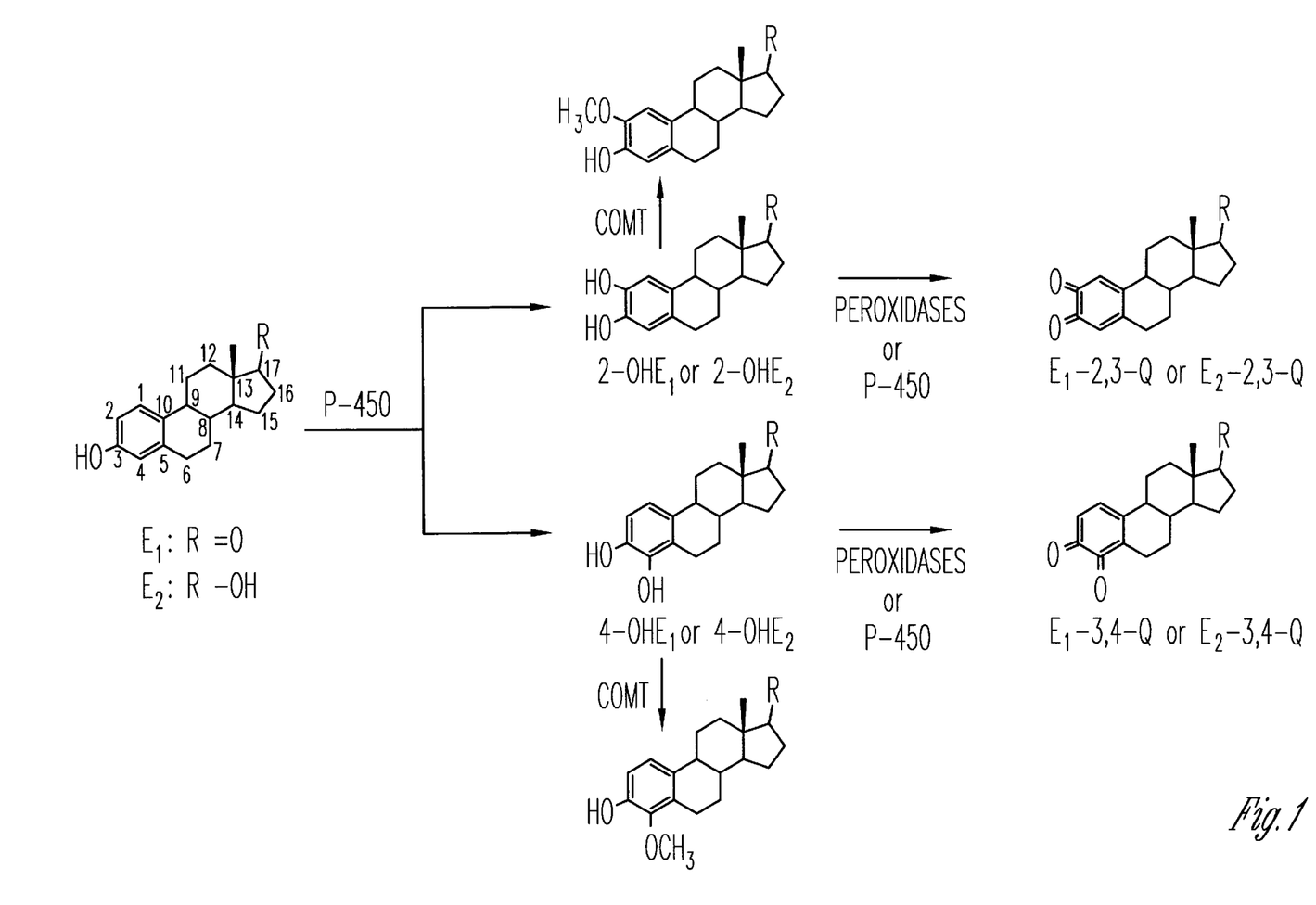
FIG. 1 is a diagram of the estrogen metabolic pathway wherein hydroxylation occurs at the 16α-position (not shown) and at the 2- or 4-position to produce catechol estrogens, which are inactivated by methylation catalyzed by catechol-O-methyltransferases (COMT) or oxidized to CE-Q by peroxidases or cytochrome P-450.
Figure 2:
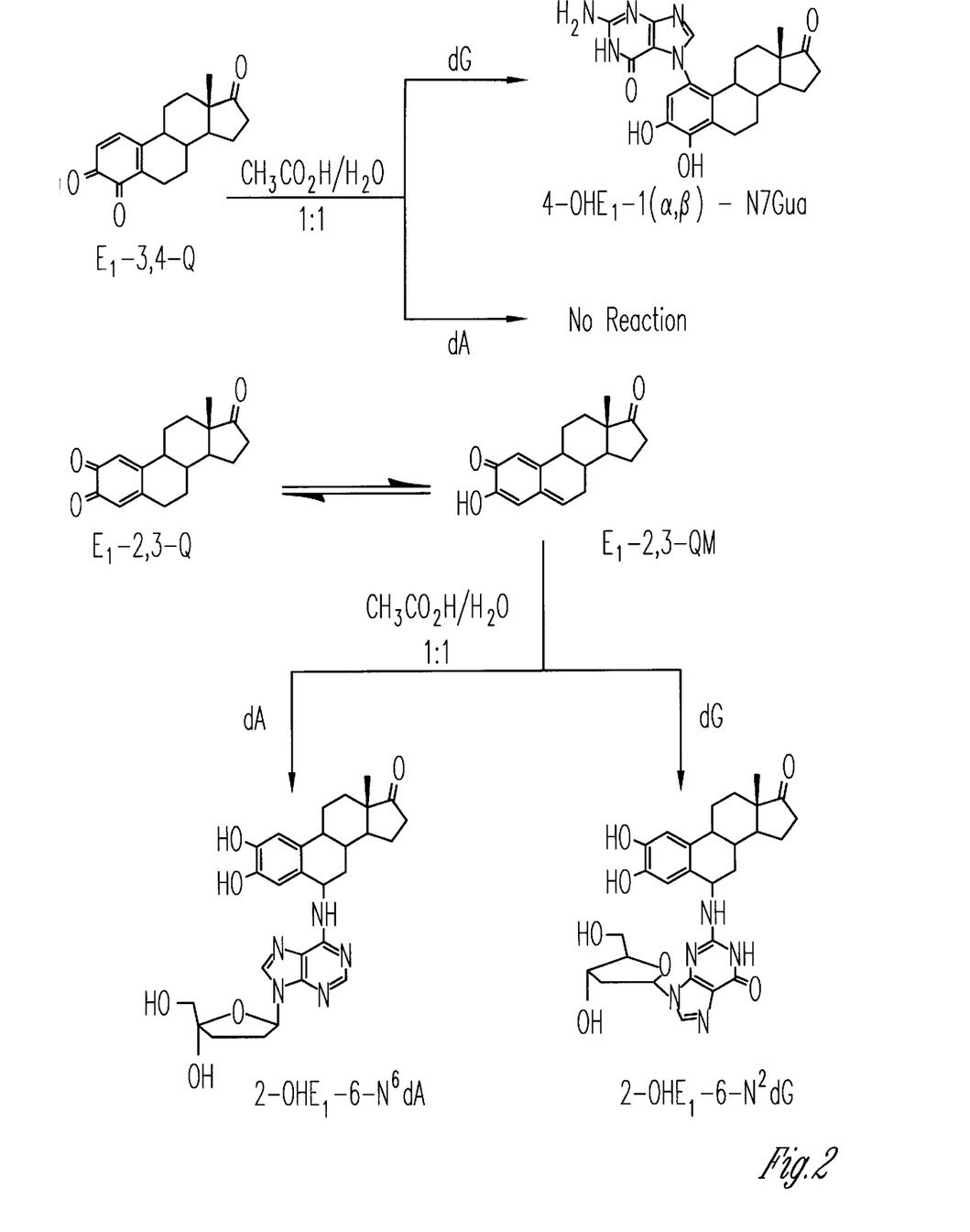
FIG. 2 is a diagram of estrogen-purine base adducts formed by the reaction of either $E_1$-3,4-Q or $E_1$-2,3-Q with either deoxyadenosine or deoxyguanosine.

Reaction of E$_1$-2,3-Q with dG yielded the product 2-OHE$_1$-6-N$^2$dG. The product is a result of 1,6-addition to the quinone after initial tautomerization of E$_1$-2,3-Q to the quinone methide (QM, FIG. 2). The reaction yield was low, ca. 10%. Reaction of E$_1$-2,3-Q with dA produced a similar product, 2-OHE$_1$-6-N$^6$dA, but in much higher yields of 80%. Recently, investigation into the isomerization of o-quinones to quinone methides has been published. The o-quinone of 2,3-dihydroxy-5,6,7,8-tetra-hydronaphthalene, in which the A, B rings are equivalent to 2-OHE$_1$, was shown to be more stable by 3.8 kcal/mol when tautomerized to the QM. Although the o-quinone is formed initially, it isomerizes to the more electrophilic QM upon standing in CH$_3$CN for extended periods of time. Calculations on thermodynamic energies of E$_1$-2,3-Q and E$_1$-2,3-QM6 shows that they are very close in energy. Molecular mechanical calculations show the QM more stable by 0.3 kcal/mol, while quantum mechanical calculations (semiempirical, PM3 Hamiltonian) reveal the o-quinone to be more stable by 1.3 kcal/mol. To study the possiblity of E$_1$-2,3-Q to E$_1$-2,3-QM tautomerization, E$_1$-2,3-Q was generated in CH$_3$CN-d$_3$ and its $^1$H-NMR spectrum was monitored over time. The inital spectrum showed the presence of only the o-quinone and the spectrum remained unchanged for two days. Even with the addition of CF3CO$_2$H-d to help catalyze the tautomerization, no change in the o-quinone spectrum was observed after standing for two weeks. This experiment indicates that in CH$_3$CN the o-quinone form of E$_1$-2,3-Q is more stable. However, reaction of E$_1$-2,3-Q with dG and dA resulted in 6-substituted products, indicating that only the E$_1$-2,3-QM-isomer, present in small quantities, reacts with these nucleosides.

Because acidic conditions were used to generate these estrogen-nucleoside adducts, an investigation was conducted of the effects of pH on the stability of both the 3,4- and 2,3-quinones. E$_1$-3,4-Q showed a marked increase in stability as the pH was lowered from 7 to 3 (Table 1), whereas E$_1$-2,3-Q did not. The 3,4- and 2,3-quinones decomposed rapidly under mildly basic conditions. Both quinones were relatively stable, with $t_{1/2}$ of 110 min at pH 7, indicating a prolonged presence if formed in vivo.

TABLE 1

Stability of E$_1$-3,4-O and E$_1$-2,3-O at Various pH

| pH[a] | $t_{1/2}$ (min)[b] | |
|---|---|---|
| | E$_1$-3,4-Q[c] | E$_1$-2,3-Q |
| 9 | <5 | <5 |
| 7 | 110 | 110 |
| 5 | 190 | 110 |
| 3 | 390 | 70 |

[a]pH was adjusted with the following buffers: pH 9, tris-HCl; pH 7, distilled H$_2$O; pH, trizma; pH 3, citric acid.
[b]$t_{1/2}$ is defined as the time when 1/2 of the original quinone concentration was observed by HPLC
[c]Quinones (0.02 mmol) were synthesized in 2 mL of CH$_3$CN and placed in 10 mL of aqueous buffer (A) 4-OHE$_1$-1($\alpha$,$\beta$)-N7Gua. In the NMR spectrum of 4-OHE$_1$-1-N7Gua, the presence of two sets of peaks indicates a mixture of two distinct chemical species. One isomer is formed in greater amount, approximately 60:40. Initially, a mixture of regioisomers at the C1 and C2 positions formed by attack of the N7 of dG was thought to account for the two chemical species. However, careful analysis by NOE showed that the N7 of guanine is bonded at the C1-position in both isomers, 4-OHE$_1$-1($\alpha$,$\beta$)-N7Gua. NOE effects between the C1 proton and the the C11 protons have been demonstrated for the parent compound, 4-OHE1, and other estrogen adducts substituted at C2. No NOE effect was seen between the resonance signals at 6.51/6.49 ppm (2-H) and other protons in the aliphatic region. Moreover, a strong NOE effect was seen between the 3-OH proton (9.44 and 9.43 ppm) and both resonance signals at 6.51 and 6.49 ppm. A significant upfield shift of several aliphatic protons, 1.10–1.21 (m, 1H), 0.74–0.98 (m, 2H), 0.45–0.68 (m, 1H), was also observed whereas the parent compound, 4-OHE$_1$, has no protons in this region (with the exclusion of the 13-CH$_3$ singlet). These protons are likely to be the ones at C11 or C12 since perpendicular attachment at C1 of the guanine ring would produce shielding to these protons. A similar upfield shift has been seen for adenine and guanine adducts at C-12 in the benz[a]anthracene compounds. In fact, substitution at N7 destabilizes the glycosidic bond, resulting in the loss of deoxyribose and its signals in the aliphatic region of the NMR spectrum. The presence of the 2-NH$_2$ proton resonance at 6.12 ppm, as well as the C-8 proton resonance at 7.90 ppm, indicates that these two nucleophilic sites in the guanine moiety are not substituted, thereby corroborating substitution at N-7. $^{13}$C NMR also confirmed the presence of two isomers. One isomer would generate 11 carbon signals in the aromatic region, but 22 were observed. In the aliphatic region, 12 signals would be seen if one isomer were present, but 19 were observed, with 5 carbon atoms of the two isomers having the same chemical shift.

Additional NOE experiments allowed not only the validation of two conformational isomers, but also assignment of the α and β forms. Molecular modeling showed that the distance between the proton on C2 and C8-Gua differs between the α and β isomers, 3.03 Å and 4.23 Å respectively. However, the distance between the protons on 3-OH and C2 are very similar, 3.60 Å and 3.62 Å, respectively. Therefore, the NOE between the protons on C2 and C8-Gua, via irradiation of the C8-Gua protons, should change the ratio of the C2 protons in the NOE difference spectrum. In contrast, the NOE effect between the protons on 3-OH and C2, via irradiation of the 3-OH protons, should be equal between the α and β isomers, and consequentially, the ratio of the C2 protons should remain unchanged. When the 3-OH proton (9.44 and 9.43 ppm) is irradiated, the NOE effect seen on the C2 protons gives the same ratio between the resonance signals at 6.51 and 6.49 ppm. When the C8-Gua proton (7.91 and 7.90 ppm) is irradiated, the ratio of the two peaks changes such that the peak at 6.49 is now the major peak, and hence belongs to the α isomer since the distance between these protons is smaller than that of the β isomer. When the C2 proton (6.51 and 6.49 ppm) is irradiated, the ratio of the 3-OH protons (9.44 and 9.43 ppm) remains unchanged, while the ratio of the C8-Gua protons (7.91 and 7.90 ppm) is reversed such that the peak at 7.91 ppm (α isomer) is predominant. thus, the major isomer is the β form.

(B) 4-$OHE_2$-1-(α,β)N7Gua. The NMR spectrum of 4-$OHE_2$-1(α,β)-N7Gua is similar to that of 4-$OHE_1$-1(α,β)-N7Gua, with the addition of signals for the 17α- proton at 4.08 ppm and the 17β-OH proton at 4.38 ppm.

(C) 2-$OHE_1$-6-$N^6$dA. Two key structural features are reflected in the NMR spectrum of 2-$OHE_1$-6-$N^6$dA. First, the presence of the aliphatic signals corresponding to the deoxyribose moiety suggests substitution at the 6-$NH_2$ position of dA, because substitution at the other two nucleophilic groups of dA, N-3 and N-7, leads to loss of the deoxyribose moiety by depurination. This is confirmed by the lack of the signals at 7.33 corresponding to the 6-$NH_2$ in dA. Instead, a doublet is found at 7.94 ppm (exchangeable with $D_2O$) that corresponds to the 6-NH group attached to the C-6 position of the 2-$OHE_1$ moiety. Evidence for substitution at C-6 is derived from the two-dimensional chemical shift correlation spectroscopy technique, which shows the C-6 proton resonance at 5.58 ppm coupled with the 6-NH(dA) proton at 7.92 ppm. Signals for both the 1- and 4-protons on the A ring are still present, further supporting the proposed structure. The protons at C-6 are prochiral, and attack of the dA nucleophile leads to a mixture of diastereoisomers in a ratio of 4:1. However, assignment of the two diastereoisomers has yet to be established.

(D) 2-$OHE_1$-6-$N^2$dG. The NMR spectrum of 2-$OHE_1$-6-$N^2$dG is similar to that of the 2-$OHE_1$-6-$N^6$dA with signals corresponding to the deoxyribose moiety, the C-1 and C-4 protons of the A ring, and the 2-NH of dG coupled to the C-6 position of the B ring. Again, attack at the prochiral C-6 results in formation of two diastereoisomers.

The catechol pathway in the metabolism of estrogens can lead to ultimate carcinogenic species, namely the catechol estrogen quinones. The reaction of $E_1$-2,3-Q, $E_1$-3,4-Q with deoxyribonucleosides has been investigated with the purpose of providing insight into the possible modes of binding of these intermediates to DNA. At the same time, authentic adducts have been prepared for use as standards in the elucidation of the structure of biologically-formed DNA adducts.

The 2,3- and 3,4-quinones display different chemistry toward the nucleophiles dG and dA. The most striking feature, with implication for DNA damage, is that the 3,4-quinones form N7Gua adducts in which the glycosidic bond of dG is destabilized, leading to formation of the $E_1$ or $E_2$-1(α,β)-N7Gua adducts. In contrast, the 2,3-quinones bind at the exocyclic amino group of dG or dA, allowing the deoxyribose moiety to remain attached to the adduct.

These results have several implications for DNA damage. First, the o-quinones of estrogens are capable of binding directly to the nucleophilic groups of DNA bases. Second, the 3,4-quinones of estrogens produce depurinating adducts that are lost from DNA, generating apurinic sites in the DNA; and third, the 2,3-quinones form stable adducts that remain bound to DNA if not repaired. In fact, reaction of 2,3- and 3,4-quinones with DNA or CE activated by horseradish peroxidase in the presence of DNA affords differential formation of stable adducts, as evidenced by 32P-postlabeling analysis. The 2,3-quinones form 10–50 times higher levels of stable adducts than the 3,4-quinones. The 3,4-quinones and the enzymically-activated 4-$OHE_1$ and 4-$OHE_2$ form almost exclusively the depurinating $E_1(E_2)$-1-(α,β)-N7Gua adducts both in vitro and in the rat mammary gland.

In the hamster kidney tumor model, 4-$OHE_1$ and 4-$OHE_2$ are carcinogenic, whereas the corresponding 2-OH isomers are not. The elevated expression of estrogen 4-hydroxylase activity in human and animal tissues susceptible to estrogen-induced tumors is a further indication that the 4-catechol pathway may be involved in tumor initiation by estrogens. The carcinogenicity of the 4-OH estrogens may be explained by the formation of depurinating adducts with the 3,4-quinones. This activity contrasts with the noncarcinogenicity of the 2-OH estrogens, which form only stable adducts. A similar relationship has been established between formation of depurinating DNA adducts by polycyclic aromatic hydrocarbons and induction of oncogenic mutations in mouse skin papillomas induced by these compounds.

EXAMPLE 2

Synthesis and Characterization of Estrogen-Mercapturate Adducts

Chemicals. 4-$OHE_1$, 4-$OHE_2$, 2-$OHE_1$, 2-$OHE_2$ and the corresponding quinones were prepared as described previously. N-acetylcysteine and cysteine were purchased from Aldrich Chem. Co. Inc.

HPLC. HPLC was performed on a Waters 600E system equipped with a Waters 990 PDA detector interfaced with an APC-IV powermate computer. analytical separations were conducted by using a YMC-ODS-AQ 5-μm, 120-Å column (6.0×250 mm) at a flow rate of 1 mL/min. For cysteine conjugates, the gradient began with 30% $CH_3OH$ in $H_2O$ for 5 min, followed by a linear gradient to 100% $CH_3OH$ in 60 min. For N-acetylcysteine conjugates, the gradient began with 25% $CH_3CN$ (0.4% TFA -trifluoracetic acid) for 5 min, followed by a 95 min linear gradient to 100% $CH_3CN$ (0.4% TFA).

Preparative HPLC was performed by using a YMC ODS-AQ 5-μm, 120-Å column (20×250 nm). The gradient for cysteine conjugates started with 40% $CH_3OH$ in $H_2O$ at flow rate of 6 mL/min for 5 min, followed by a 55 min linear gradient to 100% $CH_3OH$ at flow rate at 6 mL/min. For N-acetylcysteine conjugates, the first separation was done using the gradient starting with 30% $CH_3OH$, 5% $CH_3CH_2OH$ in $H_2O$ for 30 min at flow rate of 6 ml/min, then changed to 30% $CH_3CH_2OH$ in $H_2O$ at a flow rate of 9 mL/min in 15 min followed by a 10 min linear gradient to 50% $CH_3OH$, 50% $CH_3CH_2OH$ at a flow rate of 9 mL/min.

For N-acetylcysteine conjugates (from E-2,3-Q), the second gradient began with 35% $CH_3OH$ (0.4% TFA) in $H_2O$ (0.4% TFA) at 6 mL/min for 5 min, then a 55 min linear gradient to 100% $CH_3OH$ (0.4% TFA) at 6 ml/min.

NMR. NMR spectra were recorded in DMSC-$d_6$+TFA-d on either a Varian XL-300 or Varian XL-500. Chemical shifts are reported relative to the DMSO solvent peak (2.49 ppm).

Synthesis of the Cysteine Conjugates

4-$OHE_1$-2-Cys. To a stirred solution of cysteine (32 mg, 0.26 mmol) in 3 mL acetic acid/water (1:1 v/v), $E_1$-3,4-Q (50 mg, 0.17 mmol) in 5 mL of $CH_3CN$ was added. After 30 minutes, the reaction mixture was filtered and the product was then separated via preparative reversed phase HPLC; obtained 4-$OHE_1$-2-Cys. 59 mg, yield 85%.

$^1$H NMR: 6.90(2H,2-H,s), 3.85(1H,α-H-Cys,dd,$J_6$-4.5 Hz, $J_α$=7.5 Hz), 3.28(1H,β-H-Cys,dd,J=4.5 Hz, J=14 Hz), 3.11(1H,β-H-Cys,dd,J=8.5 Hz, J=14.5 Hz), 2.80(1H, 6-H, dd, J=5.5 Hz, J=17.5), 1.20–2.55(14H, the rest proton, m), 0.80(3H, 13-$CH_3$, s). UV: $\lambda_{max}$=292 nm. Retention time: 33.9 min. Mass: $(M^6+H)^+$ m/z 406.

4-$OHE_2$-2-Cys. In a similar manner, 4-$OHE_2$-2-Cys was obtained in 83% yield. $^1$H NMR; 6.89(1H,1-H,s), 3.85(1H, α'-H-Cys,dd,J=4.5 Hz,J=8.0 Hz), 3.49(1H,17-α-H,t,J=8.3 Hz), 3.29(1H,β-H-cys,dd,J=4.5 Hz,J=14.3), 3.11(1H,β-H-cys,J=8.0 Hz,J=14.3 Hz), 2.75(1H,6-H,dd,J=4.7 Hz,J=17.6 Hz), 1.00–2.60(14H, rest of protons, m), 0.639(3H,13-$CH_3$, s). UV: $\mu_{max}$=252 nm, 294 nm. Retention time: 30 min. Mass: $(M^6+H)^+$ m/z 408.

2-$OHE_1$-1 & 4-Cys. The two isomers: 2-$OHE_1$-1-Cys and 2-$OHE_1$-4-Cys were obtained as a mixture in 86% yield. The NMR showed the existence of the two regioisomers in the ratio 1-isomer vs. 4-isomer 3.5:1.

$^1$H NMR: 2-$OHE_1$-1-Cys (major); 6.50(1H,4-H,s); 3.84 (1H,α-H-Cys,dd,J=6.0 Hz,J=6.0 Hz); 3.17(2H,β-H-Cys,m); 1.00–2.80(15H, rest of the protons,m); 0.80(3H,13-$CH_3$).

2-$OHE_1$-4-Cys(minor); 6.80(1H,1-H,s); 3.97(1H,α-H-Cys,dd,J1=5.5 Hz,J2=5.5 Hz); 3.17(2H, β-H-Cys,m);1.00–2.80 (15H, rest of the protons, m); 0.80 (3H,13-$CH_3$,s), 3.17(2H, β-H-Cys, m); UV: $\lambda_{max}$=260 nm, 304 nm. Retention time: 33.8 min. Mass (determined as a mixture of the two isomers): $(M^++H)$ m/z 406.

2-$OHE_2$-1 & 4-Cys. Yield: 85% as mixture of the two isomers 2-$OHE_2$-1-Cys and 2-$OHE_2$-4-Cys. $^1$H NMR: (the ratio of the two isomers C-1 vs. C-4 is about 3.5:1 by comparing the 4-H vs. 1-H and the two 13-$CH_3$ signal).

2-$OHE_2$-1-Cys (major): 6.48(1H,4-H,s); 3.86(1H, α-H-Cys,dd,J=5.0 Hz,J=6.5 Hz); 3.55(1H,17-α-H,t,J=8.5 Hz); 3.16(2H,β-H-Cys,m); 0.98–2.70(15H,rest of protons,m); 0.69(3H,13-$CH_3$,s).

2-$OHE_2$-4-Cys (minor): 6.79(1H,1-H,s); 3.87(1H, α-H-Cys,dd,J=5.0 Hz,J=7.0 Hz); 3.50(1H,17-α-H,t,J=8.5 Hz); 3.16(2H, β-H-Cys,m); 6.98–2.70(15H, rest of protons, m) 0.64(3H,18-$CH_3$,s).

UV: $\lambda_{max}$=261 nm, 304 nm. Retention time: 30.4 mins. Mass: $(M^++H)$ m/z 408.

Synthesis of N-Acetylcysteine Conjugates

4-$OHE_1$-2-(NAc)Cys. To a stirred solution of N-acetylcysteine (29 mg, 0.178 mmol), in 3 ml acetic acid/water (1:1 v/v), $E_{1-3,4-Q}$ (50 mg, 0.17 mmol) in 5 ml of $CH_3CN$ was added. After 30 min, the reaction mixture was filtered and the product was separated on preparative HPLC to afford the 3-$OHE_1$-2-(N-acetyl)-cysteine 62 mg, yield 80%. $^1$H NMR: 6.77(1H,1-H,s), 4.27(1H,(α-H-Cys,dd,J1= 4.38, J2=8.79), 3.14(1H,β-H-Cys,dd,J1=4.38, J3=13.35), 2.93(1H,β-H-Cys,dd,J2=8.85, J3=13.55), 2.78(1H,6-H,dd,J, J), 1.10–2.60(14 H,m), 1.82(3H,N-acetyl-$CH_3$,s), 0.754(3H, 18-$CH_3$,s).

UV: $\lambda_{max}$=292 nm. Retention time: 32.8 min. Mass: $(M^++H)$ m/z 448.

4-$OHE_2$-2-(NAc)Cys: Similarly, 4-OHE2-2-(NAc)Cys was obtained in 79% yield. $^1$H NMR: 6.74(1H,1-H,s), 4.24(1H,α-H-Cys,dd,J1=4.7, J2=9.3), 3.49(1H,t,17-α-H,J= 8.8), 3.13(1H,β-H-Cys,dd,J1=5, J3=14), 2.91(1H,β-H-Cys, dd,J2=9, J3=13.4), 2.73(1H,6-H),dd,J,J), 1.832(3H,N-acetyl-$CH_3$,s), 1.00–2.60(14H,rest protons,m), 0.64(3H,18-$CH_3$,s).

UV: $\lambda_{max}$=254 nm, 292.8 nm. Retention time: 30.4 min. Mass: $(M^++H)$ m/z 450.

2-$OHE_1$-1-(NAc)Cys & 2-$OHE_1$-4-(NAc)Cys. Similarly, 2-$OHE_1$-1-(NAc)Cys and 2-$OHE_1$-4-(NAc)Cys were obtained in a total of 76% yield. Then acetic gradient was used to separate the two isomers (1-isomer: 4-isomer= 2.23:1).

2-$OHE_1$-1-(NAc)Cys: $^1$H NMR: 6.48(1H,4-H,s), 3.68 (1H,α-H-Cys,dd,J=,J=), 3.22(1H,β-H-cys,dd,J=,J=), 2.65 (2H,β-H-Cys and 6-H,m), 1.05–2.60(14H,m), 1.77(3H,N-acetyl-$CH_3$,s), 0.83(3H,18-$CH_3$,s). UV: $\lambda_{max}$=261.6 nm, 304.4 nm. Retention time: 30.85 min. Mass: $(M^++H)$ m/z 448.

2-$OHE_1$-4-(NAc)Cys: $^1$H NMR: 6.75(1H,1-H,s), 4.15 (1H,α-H-Cys,dd,J=,J=), 3.15(1H,β-H-Cys,dd,J=,J=), 2.95 (2H,β-H-Cys and 6-H,m), 1.15–2.65(14H,m), 1.81(3H,N-acetyl-$CH_3$,s), 0.794(3H,18-$CH_3$,s). UV: $\lambda_{max}$=258 nm, 302.4 nm. Retention time: 33.3 min. Mass: $(M^++H)$ m/z 448.

2-$OHE_2$-1-(NAc)Cys & 2-$OHE_2$-4-(NAc)Cys. 2-$OHE_2$-1-(NAc)Cys and 2-$OHE_2$-4-(NAc)Cys were obtained in 77% yield. Further separation gave the two isomers. (1-isomer: 4-isomer=1.95).

2-$OHE_2$-1-(NAc)Cys: 1H NMR: 6.45(1H,4-H,s), 3.63 (1H,α-H-Cys,dd,J=,J=), 3.49(1H,t,17-α-H,J=), 3.21(1H,β-H-Cys,dd,J=,J=), 2.60(2H,βH-Cys and 6-H,m), 0.95–2.55 (14 rest protons,m), 1.82(3H,N-acetyl-$CH_3$,s), 0.674(3H,18-$CH_3$,s). UV: $\lambda_{max}$=261.6 nm, 304 nm. Retention time: 25.96 min. Mass: $(M^++H)$ m/z 450.

2-$OHE_2$-4-(NAc)Cys. $^1$H NMR: 6.74(1H,1-h,s), 4.13(1H, α-H-Cys,dd,J=,J=), 3.50(1H,t,17-α-H,J=), 3.21(1H,β-H-Cys,dd,J=,J=), 2.92(2H,β-H-Cys and 6-H,m), 1.00–2.70(14 H,m), 1.81(3H,N-acetyl-$CH_3$,s), 0.65(3H,18-$CH_3$,s). UV: $\lambda_{max}$=259.6 nm, 302.8 nm. Retention time: 29.6 min.

EXAMPLE 3

Preparation of Estrogen Adduct Fluorescent Probes

To the 4-OHE1-1(α,β)-N7Gua (ca. 5 mg) contained in a 50-mL glass stoppered Erlenmeyer flask, 10 mL of dansyl chloride solution and 15 mL of basic solution were added in succession. The dansyl chloride solution consisted of 5 mg/mL in acetone while the basic solution consisted of 0.367 g of sodium carbonate in 300 mL of water. After dissolving the sample with swirling, the flask was stoppered and allowed to stand in the dark at room temperature for 2 h. The product was then isolated via HPLC: 3-OH,4-OH, $N^2$Gua-tridansyl-$E_1$-1(α,β)-N7Gua as set forth in Formula 3A.

EXAMPLE 4

Preparation of Immunogenic Conjugates

In one embodiment, the adduct/hapten is linked to the carrier via a rigid heterofunctional spacer moiety of about 12 angstroms (MCC ester) or a structurally less complex heterobifunctional spacer moiety of about 8 angstroms (PDP ester). This enhances recognition of the hapten by the immune system of the antibody-producing host. When the carrier is a protein, such as hen egg albumin, it is also preferred to carry out the conjugation reaction in an environment, such as 20–50% DMSO in an aqueous buffer, that promotes dissolution of the hydrophobic adduct and thereby reduces sequestration of the PAH adduct in hydrophobic regions of the carrier. A conjugate complex with about 20 to 50 molecules of the adduct per 100,000 daltons of carrier has been found to be an effective immunogen, particularly for the production of monoclonal antibodies (MAbs).

EXAMPLE 5

Preparation of Adduct-Specific Antibody Capture Complexes

In one embodiment the adduct/hapten is linked to the adhesion molecule (generally a protein) via a rigid heterobifunctional spacer moiety of about 12 angstroms (MCC ester) or a structurally less complex heterobifunctional spacer moiety of about 8 angstroms (PDP ester). This enhances recognition of the hapten by hapten-specific antibodies. When the adhesion molecule is a protein, such as bovine serum albumin (BSA), it is also preferred to carry out the coupling reaction in an environment, such as 20–50% DMSO in an aqueous buffer, that promotes dissolution of the hydrophobic adduct and thereby reduces sequestration of the PAH adduct in hydrophobic regions of the protein. A conjugate complex with between about 5 and about 10 molecules of adduct/hapten per molecule of BSA has been found to be an effective capture complex in both a screening ELISA for detection of adduct-specific monoclonal antibodies and in a competitive ELISA for detection of free adduct/hapten.

In conclusion, the adducts described here provide insight into the type of DNA damage possible when CE-Q are generated in vitro and in vivo and will be used in studies designed to elucidate the structure of estrogen adducts in biological systems.

The above description thus sets forth novel estrogen-nucleoside and estrogen-mercapturate adducts as well as diagnostic assays for quantitation of the adducts. It further demonstrates a novel series of monoclonal antibodies which are useful for detecting the natural and synthetic adducts described herein. It is therefore submitted that the present invention accomplishes at least all of its stated objectives.

What is claimed is:

1. A method of concentrating and purifying an adduct of an estrogen and a purine isolated from biolgical sources, wherein the adduct is selected from the group consisting of 7[4-hydroxyestron-1($\alpha,\beta$)-yl]guanine, 7[4-hydroxyestradiol-1($\alpha,\beta$)-yl]guanine, $N^2$[2-hydroxyestron-6-yl]deoxyguanosine, $N^2$[2-hydroxyestradiol-6-yl]deoxyguanosine, $N^6$[2-hydroxyestron-6-yl]deoxyadenosine, and $N^6$[2-hydroxyestradiol-6-yl]deoxyadenosine, comprising:

covalently coupling anti-adduct antibodies, which selectively bind to said adducts of an estrogen and a purine, to a solid matrix to form bound anti-adduct antibodies, wherein the matrix is derivatized with couplers selected from the group consisting of CNBr, N-hydroxysuccinimide, and hydrazide;

applying a sample from the biological sources to the solid matrix-anti-adduct antibodies, so that said adducts of an estrogen and a purine bind selectively to the anti-adduct antibodies;

washing the solid matrix-anti-adduct antibodies, to which said adducts of an estrogen and a purine bind; and, eluting the adducts.

2. A method according to claim 1 wherein the solid matrix is agarose gel.

3. A method according to claim 2 wherein the agarose gel is in the form of beads and further providing that the beads are from about 50–200$\mu$ in diameter.

4. A method according to claim 1 wherein the biological source is selected from the group consisting of human serum, tissues, tissue extracts, urine and other bodily fluids.

* * * * *